United States Patent
Yoneda (10) Patent No.: US 9,330,457 B2
(45) Date of Patent: May 3, 2016

(54) DEVICE, METHOD, AND PROGRAM FOR ANALYZING A MAGNETIC RESONANCE IMAGE USING PHASE DIFFERENCE DISTRIBUTION

(71) Applicant: NATIONAL UNIVERSITY CORPORATION KUMAMOTO UNIVERSITY, Kumamoto (JP)

(72) Inventor: Tetsuya Yoneda, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 124 days.

(21) Appl. No.: 14/347,703

(22) PCT Filed: Sep. 26, 2012

(86) PCT No.: PCT/JP2012/074701
§ 371 (c)(1),
(2) Date: Mar. 27, 2014

(87) PCT Pub. No.: WO2013/047583
PCT Pub. Date: Apr. 4, 2013

(65) Prior Publication Data
US 2014/0233825 A1    Aug. 21, 2014

(30) Foreign Application Priority Data

Sep. 28, 2011 (JP) ................................. 2011-213535

(51) Int. Cl.
*G06K 9/00* (2006.01)
*G06T 7/00* (2006.01)
(Continued)

(52) U.S. Cl.
CPC ............... *G06T 7/0012* (2013.01); *A61B 5/055* (2013.01); *A61B 5/4088* (2013.01); *G01R 33/56* (2013.01); *G01R 33/5608* (2013.01); *G01R 33/24* (2013.01); *G06T 2207/30004* (2013.01)

(58) Field of Classification Search
None
See application file for complete search history.

(56) References Cited

U.S. PATENT DOCUMENTS

| 5,909,119 A | 6/1999 | Zhang et al. |
| 2005/0020904 A1 | 1/2005 | Cline et al. |
| 2008/0119721 A1 | 5/2008 | Kimura et al. |

FOREIGN PATENT DOCUMENTS

| EP | 2 380 492 A1 | 10/2011 |
| JP | 2004-344327 A | 12/2004 |

(Continued)

OTHER PUBLICATIONS

International Search Report for corresponding International Application No. PCT/JP2012/074701, mailed Oct. 30, 2012 (2 pages).

(Continued)

*Primary Examiner* — Atiba O Fitzpatrick
(74) *Attorney, Agent, or Firm* — Osha Liang LLP (57) ABSTRACT

An image analysis device for analyzing a magnetic resonance image obtained from a living body includes a phase difference distribution creating unit configured to create a phase difference distribution of a magnetic resonance image obtained from a predetermined area of the living body, a fitting unit configured to fit the phase difference distribution created by the phase difference distribution creating unit with a plurality of function groups, and a verifying unit configured to verify normality of the living body included in the predetermined area, based on the magnetic susceptibility of the tissue included in the predetermined area determined on the basis of the parameters of the plurality of function groups fit to the phase difference distribution by the fitting unit.

6 Claims, 7 Drawing Sheets

(51) Int. Cl.
*A61B 5/055* (2006.01)
*A61B 5/00* (2006.01)
*G01R 33/56* (2006.01)
*G01R 33/24* (2006.01)

(56) References Cited

FOREIGN PATENT DOCUMENTS

| JP | 2005-28151 A | 2/2005 |
| JP | 2009-125582 A | 6/2009 |
| WO | 2010/073923 A1 | 7/2010 |

OTHER PUBLICATIONS

Yoneda, T. et al.; "Triple-layer Appearance of Human Cerebral Cortices on Phase-Difference Enhanced Imaging using 3D Pinciple of Echo Shifting with a Train of Observations (PRESTO) Sequence;" Proceedings of International Society for Magnetic Resonance in Medicine; Apr. 18, 2009 (1 page).

Kakeda, S. et al.; "A novel tract imaging technique of the brainstem using phase difference enhanced imaging: normal anatomy and initial experience in multiple system atrophy;" European Radiology; vol. 21, Issue 10, pp. 2202-2210; Oct. 1, 2011 (9 pages).

Extended European Search Report for corresponding European Patent Application No. 12836937.8 issued Mar. 26, 2015 (11 pages).

Kathryn E. Hammond, et al. "Development of a robust method for generating 7.0 T multichannel phase images of the brain with application to normal volunteers and patients with neurological diseases", NeuroImage 39 (2008) pp. 1682-1692, XP22450340A (11 pages).

Bing Yao, et al. "Susceptibility contrast in high field MRI of human brain as a function of tissue iron content", NeuroImage 44 (2009), pp. 1259-1266, XP25770338A (8 pages).

Robert Zivadinov, et al. "Abnormal subcortical deep-gray matter susceptibility-weighted imaging filtered phase measurements in patients with multiple sclerosis", A case-control study, NeuroImage 59 (2012) pp. 331-339, XP28120189A (9 pages).

Andrew J. Walsh, et al. "Susceptibillity phase imaging with comparison to R2 mapping of iron-rich deep grey matter", NeuroImage 57 (2011), pp. 452-461, XP28296839A (10 pages).

E. M. Haacke, et. al, Physics Review, "Susceptibility-Weighted Imaging: Technical Aspects and Clinical Applications, Part 1", AJNR Am J Neuroradiol 30:19-30, Jan. 2009 (12 pages).

Masaya Takahashi, et al., "Relationship between cancellous bone induced magnetic field and ultrastructure in a rat ovariectomy model", Magnetic Resonance Imaging 18 (2000) 33-39, XP55177497A (7 pages).

E. Mark Haacke, PhD, et al., "Establishing a Baseline Phase Behavior in Magnetic Resonance Imaging to Determine Normal vs. Abnormal Iron Content in the Brain", Journal of Magnetic Resonance Imaging 26:256-264 (2007), XP55177499A (9 pages).

Office Action issued in corresponding Australian Patent Application No. 2012317518 dated Jan. 7, 2015 (4 pages).

DEVICE, METHOD, AND PROGRAM FOR ANALYZING A MAGNETIC RESONANCE IMAGE USING PHASE DIFFERENCE DISTRIBUTION

TECHNICAL FIELD

The present invention relates to an image analysis device, an image analysis method, and an image analysis program, and more particularly, to an image analysis device, an image analysis method, and an image analysis program for analyzing a magnetic resonance image obtained from a living body.

BACKGROUND ART

An Alzheimer's disease which is one of dementia is the current major problem, and has been studied in the world without exception. One of main causes of the Alzheimer's disease is known as a protein called amyloid β accumulated in the brain. However, a diameter of the amyloid β is about 0.1 mm or less, and it is considered that the amyloid β cannot directly be portrayed by means of a current image detecting device for health care services.

By the way, most of medical imaging equipment such as an MRI is aimed at directly portraying a target tissue or lesions. However, in the medical field, there is a limitation of an imaging time, and there is a limitation of the resolution in the image which can be imaged within the limited time. Under the limitation, the target tissue or the lesions cannot be directly portrayed. Of course, in high-resolution image equipment, the portraying is possible, but the high-resolution image equipment is beyond a range of the health care services, and expensive.

Of course, in the case of using a superhigh magnetic MRI (for example, MRI of 7 Tesla and the like), direct portraying is possible, but the superhigh magnetic MRI is beyond the range of the health care services provided under medical insurance. An image diagnosis method requiring expensive equipment which is beyond the range of the health care services provided under medical insurance cannot be said as the solution of a current urgent medical problem, and a method of detecting a tissue or lesions, which cannot be portrayed by means of medical imaging equipment such as an MRI, realistically within a current range of health care services provided under medical insurance has been required.

For this reason, for example, the MR system disclosed in Patent Document 1 images a high-resolution MR image with a magnetic field strength of 3 tesla or more by using a 3D inclined double echo pulse sequence, and collects image data of the MR image for two different echo times so that a 3D phase image is collected.

In addition, in order to measure a predetermined component and a linear component regarding nonuniformity of the magnetic field, since a smoothing spherical harmonic function is subtracted from the measured value collected between the MRIs to obtain a local change of the magnetic field in the area of interest. Since ability to measure a magnetic field variation in the brain by the MRI is increased according to the square of B0, measurement of magnetism and iron of the brain is more sensitive according to the technique disclosed in the Patent Document 1.

CITATION LIST

Patent Literature

Patent Document 1: Japanese Patent Application Laid-Open No. 2005-28151

However, the technique disclosed in the aforementioned Patent Document 1 has an intention of increasing the entire sensitivity in the MRI, and only, directly portraying the MR image. Further, it is unclear whether a tissue or lesions, which cannot be portrayed by means of medical imaging equipment such as an MRI, is detected within the current range of health care services provided under medical insurance. In addition, the MRI which does not adopt the technique disclosed in the aforementioned Patent Document 1 cannot achieve the improved sensitivity.

One or more embodiments of the present invention provide an image analysis device, an image analysis method, and an image analysis program which can detect a tissue or lesions, which cannot be portrayed by means of medical imaging equipment such as an MRI, realistically within a current range of health care services.

SUMMARY OF THE INVENTION

One or more embodiments of one aspect of the present invention may provide an image analysis device for analyzing a magnetic resonance image obtained from a living body, including: a phase difference distribution creating unit configured to create a distribution of phase difference or phase (Hereinafter, "phase difference" and "phase" are uniformly referred to as "phase difference") of a magnetic resonance image obtained from a predetermined area of the living body; a fitting unit configured to fit the phase difference distribution created by the phase difference distribution creating unit with a plurality of function groups; and a verifying unit configured to verify normality of the living body included in the predetermined area, on the basis of the magnetic susceptibility of the tissue included in the predetermined area determined on the basis of the parameters of the plurality of function groups fit to the phase difference distribution by the fitting unit.

Further, the aforementioned image analysis device includes various forms to be embedded in other devices, or implemented together with other methods, and the like. Further, the present invention may be implemented by an image analysis system including the image analysis device, an image analysis method having a process corresponding to the configuration of the aforementioned device, an image analysis program implementing a function corresponding to the configuration of the aforementioned device in a computer, a recording medium readable by the computer recoding the image analysis program.

As described above, according to one or more embodiments of the present invention, a minute change in tissue may be detected by using an MRI phase difference image which is sensitive to a minute magnetic change of the tissue. In other words, a phase change due to a partial volume effect of the tissue is determined as a change in phase difference distribution of a predetermined target area (in one or more embodiments below, referred to as an area of interest), and as a result, existence of the target tissue may be stably verified by using an MRI which has a short imaging time and low magnetic field intensity.

Instead of directly creating an image of pixel by pixel having high accuracy by an unrealistic method for a long imaging time, it is considered that a detecting method using short-time imaging or low-magnetic field equipment is facilitated in the industry and the medical field. Further, the method may be used without changing a device in the related art or introducing an additional device because of software processing.

DETAILED DESCRIPTION OF EMBODIMENTS

In embodiments of the invention, numerous specific details are set forth in order to provide a more thorough understanding of the invention. However, it will be apparent to one with ordinary skill in the art that the invention may be practiced without these specific details. In other instances, well-known features have not been described in detail to avoid obscuring the invention.

Hereinafter, embodiments of the present invention will be described according to the following order.
(1) Configuration of embodiments:
(2) Creating phase difference image:
(3) Determining process:
(4) Creating of shape image:
(5) Summary:

(1) Configuration of Embodiments

Figure 1:
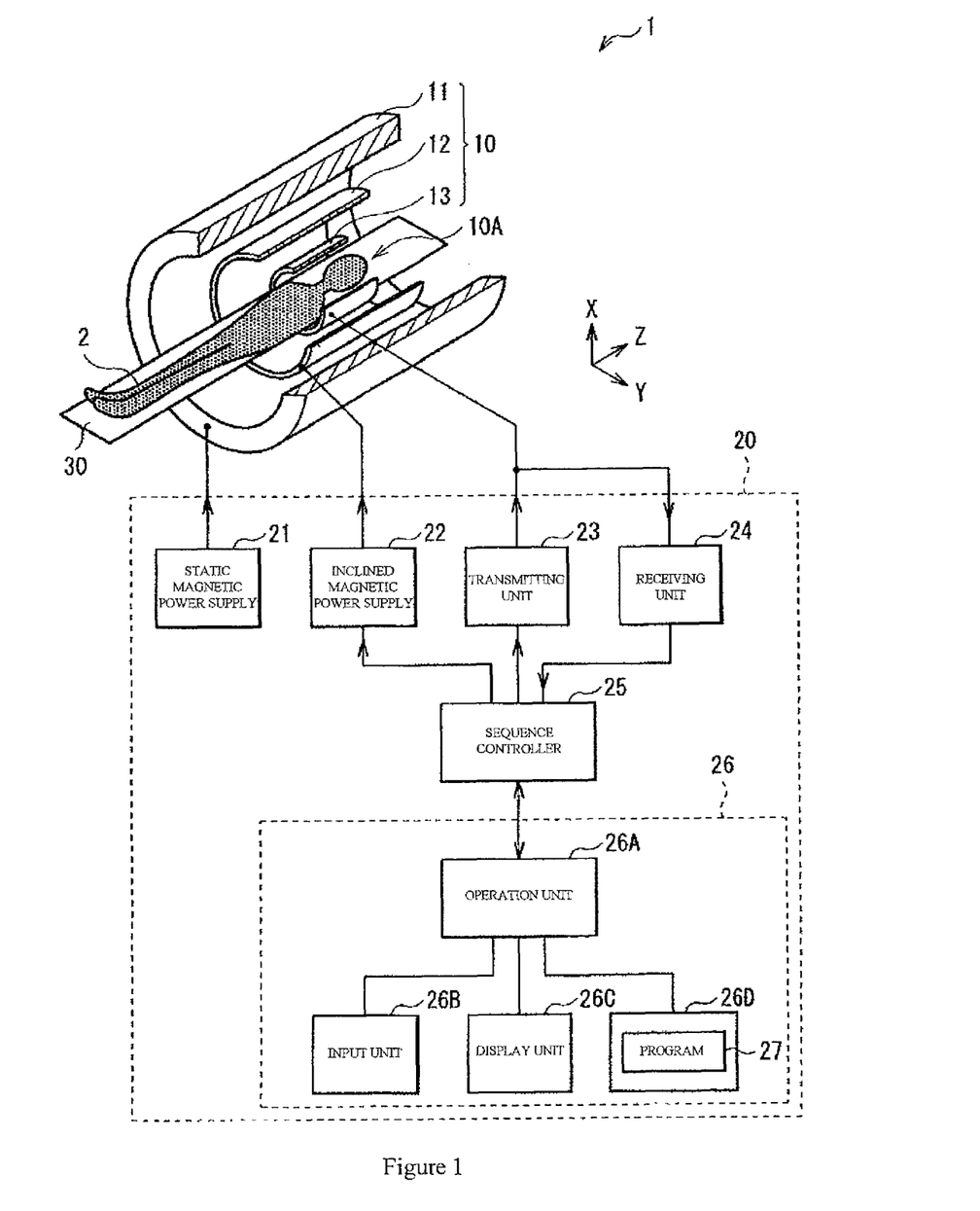
FIG. 1 is a diagram illustrating a schematic configuration of a magnetic resonance imaging (MRI) device according to one or more embodiments.

FIG. 1 is a diagram illustrating a schematic configuration of a magnetic resonance imaging (MRI) device 1. The MRI device 1 is a device of imaging internal information of a subject 2 by using an NMR phenomenon. The MRI device 1 is a new type MRI device that portrays a shape image by using a phase image imaging a rotation angle of a magnetization vector in addition to an intensity image imaging an intensity component of a magnetic resonance signal (MR signal), as a magnetic resonance image (MR image). Further, in one or more embodiments, the MRI device 1 and one of a control system 20 and an information processing device 26 to be described below configure the image analysis device.

The MRI device 1 illustrated in FIG. 1 includes a coil system 10 and a control system 20.

[Coil System 10]

The coil system 10 includes, for example, a static magnetic coil portion 11, an inclined magnetic coil portion 12, and a radio frequency (RF) coil portion 13. The coil portions have, for example, substantially cylindrical shapes, and are disposed so that central axes (not illustrated) are the same as each other. A bed portion 30 supporting the subject 2 is disposed in a plane including the central axes.

The bed portion 30 is disposed in a bore 10A (internal space) of the coil system 10. The subject 2 on the bed portion 30 is carried in or out the bore 10A by moving the bed portion 30 by means of a carrying means (not illustrated). Further, in one or more embodiments, as illustrated in FIG. 1, a direction parallel with the central axis is represented as a Z axis, and two directions which are perpendicular to the Z axis and perpendicular to each other are represented as an X axis and a Y axis.

The static magnetic coil portion 11 generates a static magnetic field in the bore 10A. The static magnetic coil portion 11 is configured by, for example, a superconductive coil, a normal conductive coil, or the like. A direction of the static magnetic field generated by the static magnetic coil portion 11 is substantially parallel with the Z-axial direction. Further, in FIG. 1, an example in which a body-axial direction of the subject 2 is parallel with the direction of the static magnetic field is described, but the body-axial direction may be perpendicular to the direction of the static magnetic field.

The inclined magnetic coil portion 12 generates an inclined magnetic field (gradient magnetic field), for example, in three axes which are vertical to each other, that is, slide-axial, phase-axial, and frequency-axial directions. The inclined magnetic coil portion 12 is configured by three kinds of coils, for example, a slide-axial coil, a phase-axial coil, and a frequency-axial coil. In this case, any of the X axis, the Y axis, and the Z axis may be a slide axis. For example, when the Z axis is the slide axis, the X axis may be the phase axis, and the Y axis may be the frequency axis.

Further, the MR signal may be collected even in a coordinate system (for example, polar coordinate system) in addition to the above Cartesian coordinate system, and when the MR signal is collected in the coordinate system, a proper axis (for example, a radial direction and an angular direction) is set in the coordinate system.

Figure 2:
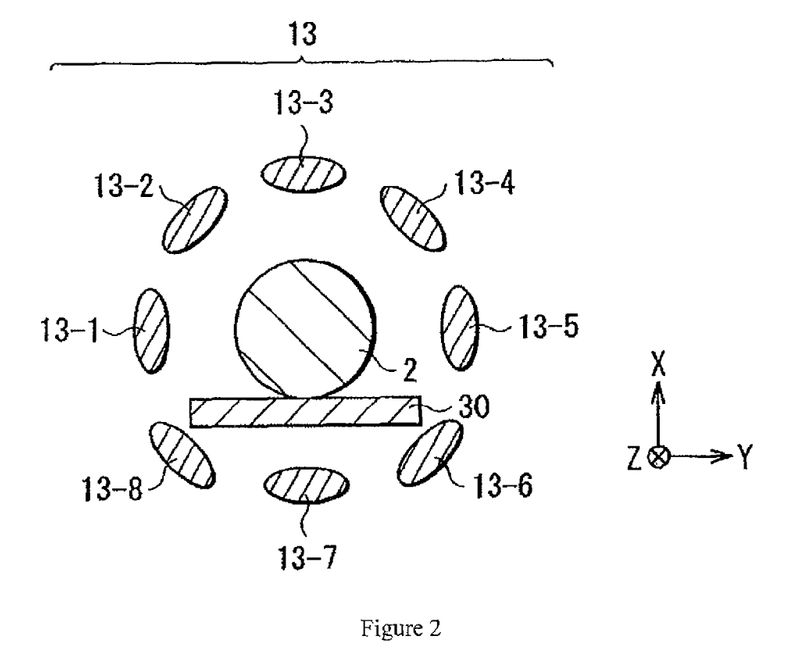
FIG. 2 is a cross-sectional configuration diagram illustrating a modified example of an RF coil portion according to one or more embodiments.

The RF coil portion 13 generates an RF magnetic field exciting a spin of the subject 2 in a static magnetic space and receives the MR signal generated according the spin excited by the RF magnetic field. Further, a coil receiving the MR signal in the RF coil portion 13 may be used together with a coil generating the RF magnetic field, or may be installed separately from the coil generating the RF magnetic field. Further, the RF coil portion 13 may be configured by a single coli, or for example, a plurality of coils 13-1 to 13-8 (multi-channel) as illustrated in FIG. 2. Further, when the RF coil portion 13 is configured by the multi-channel, the RF coil portion 13 may obtain the MR signal for each channel.

The MR signal is obtained by, for example, a pulse sequence of a gradient echo (GE), and becomes a sampling signal for a frequency domain, that is, a Fourier space (k space). The GE system includes, for example, a steady state, in addition to the GE. Further, the pulse sequence may be, for example, a balanced steady state free precession (SSFP) and a true fast imaging with steady-state precession (TrueFISP), and may be a spin echo (SE) and the like which are not the GE.

[Control System 20]

The control system 20 includes, for example, a static magnetic power supply 21, an inclined magnetic power supply 22, a transmitting unit 23, a receiving unit 24, and a sequence controller 25, as illustrated in FIG. 1.

The static magnetic power supply 21 supplies power to the static magnetic coil portion 11 and drives the coil system 10. When the power is supplied to the static magnetic coil portion 11, the static magnetic field is generated in the bore 10A. The inclined magnetic power supply 22 supplies the power to the inclined magnetic coil portion 12 according to a control signal input from the sequence controller 25. A desired inclined magnetic field (gradient magnetic field) is generated in the slide-axial, phase-axial, frequency-axial directions by supplying the power to the inclined magnetic coil portion 12, respectively.

The transmitting unit 23 applies the RF signal to the RF coil portion 13 according to the control signal input from the sequence controller 25.

The receiving unit 24 receives the MR signal generated by driving the coil system 10. For example, the MR signal received from the RF coil portion 13 is detected to generate complex data (raw data) which is digitalized by performing necessary signal processing and analog-to-digital (A/D) converting. Of course, the receiving unit 24 directly A/D-converts the detected MR signal to generate the raw data. The raw data generated by the receiving unit 24 is output to, for example, the sequence controller 25.

The sequence controller 25 drives the inclined magnetic power supply 22 for driving the MRI device 1, the transmitting unit 23, and the receiving unit 24. For example, the sequence controller 25 drives the inclined magnetic power supply 22, the transmitting unit 23, and the receiving unit 24 by applying the control signal to the inclined magnetic power supply 22, the transmitting unit 23, and the receiving unit 24.

The control signal is generated according to the pulse sequence defining a size, an applying time, and an applying timing and the like of a pulse current applied to the inclined magnetic power supply 22, the transmitting unit 23, and the receiving unit 24. Information on the pulse sequence is input to the sequence controller 25 from the information processing device 26 to be described below. Further, the sequence controller 25 outputs the raw data input from the receiving unit 24 to the information processing device 26.

The control system 20 further includes the information processing device 26 as illustrated in FIG. 1. The information processing device 26 includes, for example, an operation unit 26A, an input unit 26B, a display unit 26C, and a memory unit 26D.

The input unit 26B is a device which inputs user's information to the inside of the information processing device 26 as digital data, and for example, configured by a keyboard, a mouse, a scanner, or the like.

The display unit 26C displays a result (for example, shape image) processed by the operation unit 26A, a dialog for inputting data such as an imaging condition, or the like, and for example, is configured by a display device such as a liquid crystal display.

The memory unit 26D stores various programs controlling the MRI device 1, and for example, a program 27 used for a determination process to be described below, a phase difference enhancement imaging program and the like which are used to create the shape image to be described below, or the like.

The operation unit 26A analyzes and executes commands of various programs, and for example, is configured by a central processing unit (CPU). In the operation unit 26A, the program 27 stored in the memory unit 26D is loaded at the same time of starting the MRI device 1, and as a result, the operation unit 26A analyzes and executes the command of the program 27 according to a user's instruction.

Further, the operation unit 26A may be configured by hardware corresponding to functions of the various programs (for example, the program 27). Hereinafter, various commands of the program 27 are executed in the operation unit 26A to create the phase image.

(2) Creating Phase Difference Image

Next, creation of the phase difference image performed in the MRI device 1 will be described. In order to obtain the phase difference image, the intensity image and the phase image are required. The images may be obtained by using the pulse sequence of the GE, but may use, for example, another pulse sequence included in the GE system or a pulse sequence other than the GE system.

The phase image obtained by the pulse sequence of the GE system is proportional to the product $\Delta B \times TE$ of a change amount $\Delta B$ of a local magnetic field (local magnetic field as compared with an external magnetic field) made by the tissue included in each pixel and an echo time TE required for imaging. Accordingly, in order to extract large phase (difference) information from the phase image, the TE is increased, or a function enhancing the $\Delta B$ (so-called an enhancement function is changed to be stronger.

In detail, the imaging is performed by using a predetermined pulse sequence. The number of imaging may be once, and may be several times for statistical processing. Further, in the case where the RF coil portion 13 is configured by the multi-channel to obtain the MR signal for each channel, an arithmetic mean of the MR signals obtained for each channel is calculated, and the intensity image and the phase image are created by using the arithmetic mean of the MR signals. Further, when the arithmetic mean is calculated, sensitivity correction for each MR signal may be performed in advance.

(Obtaining Raw Data R)

Figure 3:
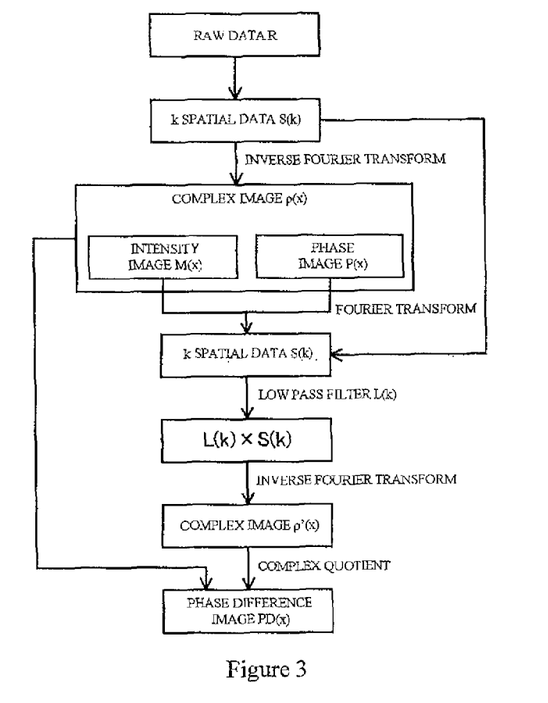
FIG. 3 is a diagram illustrating a flow of data processing until a phase difference image is created according to one or more embodiments.

FIG. 3 is a diagram illustrating a flow of data processing until a phase difference image is created. The data processing illustrated in FIG. 3 is performed in the control system 20 under the control of the operation unit 26A. The operation unit 26A receives the user's instruction to start an operation of the data processing illustrated in the drawing.

First, the operation unit 26A outputs a control signal requesting to obtain the raw data by using the predetermined pulse sequence to the sequence controller 25. Then, the control signal according to the predetermined pulse sequence is output from the sequence controller 25 to the inclined magnetic power supply 22, the transmitting unit 23, and the receiving unit 24.

When the control signal is input, the inclined magnetic power supply 22 and the transmitting unit 23 output a predetermined current pulse to the coil system 10, and the RF coil portion 13 detects the MR signal. Here, the detected MR signal is converted into the raw data R by the predetermined signal processing in the receiving unit 24.

The receiving unit 24 inputs the raw data R to the sequence controller 25, and the sequence controller 25 transmits (inputs) the raw data R to the operation unit 26A. As such, the operation unit 26A obtains the data (the raw data R) corresponding to the MR signal.

(Creating Intensity Image M(x) and Phase Image P(x))

Next, the operation unit 26A is disposed in a k space in which the raw data R input from the sequence controller 25 is set in an internal memory (not illustrated). Hereinafter, the data disposed in the k space is referred to as a k spatial data S(k).

The operation unit 26A performs inverse Fourier transform with respect to the k spatial data S(k), and reconfigures a complex image ρ(x). The complex image ρ(x) is an image in which a real image exists in a real part and an imaginary image exists in an imaginary part, as illustrated in the following Equation 1.

[Equation 1]

$$\rho(x) = |\rho(x)| e^{i\theta(x)} \quad (1)$$

The operation unit 26A obtains an intensity image M(x) and a phase image P(x) from the complex image ρ(x).

(Creating Phase Difference Image PD(x))

In one or more embodiments, when the MR signal is obtained, a long TE is used. Accordingly, phase wrapping occurs in the phase image P(x), and the phase exceeds 2π to obtain a phase value obtained by subtracting 2 πn (n is an integer) form a real phase. As a result, the phase image P(x) becomes a stripe image and thus does not have an original phase value. In this case, the operation unit 26A removes the phase wrapping and simultaneously, performs a process for extracting the phase difference.

In detail, the operation unit 26A, first, performs Fourier transform with respect to the complex image ρ(x), and returns the complex image ρ(x) to the k spatial data S(k). In addition, the operation unit 26A reads the k spatial data S(k) disposed in the k space. Next, the operation unit 26A performs inverse Fourier transform for data L(k)×S(k) obtained through a low pass filter (LPF) with respect to the k spatial data S(k) to obtain a complex image ρ'(x). Further, the L(k) is a function of the LPF.

Next, the operation unit 26A creates a phase difference image PD(x) by using the complex images ρ(x) and π'(x). In detail, the operation unit 26A performs a complex quotient operation that divides the complex image ρ(x) by the complex image ρ'(x) to create the phase difference image PD(x). Accordingly, the phase wrapping of the phase portion is removed.

In this case, the phase difference included in the phase difference image PD(x) has a width of 2π, and in one or more embodiments, the phase difference included in the phase difference image PD(x) is assumed as −π≤PD(x)<π. A sign of the phase difference included in the phase difference image PD(x) is determined by −γ×ΔB×TE.

However, the sign of the phase difference included in the phase difference image PD(x) may be changed by changing definition of the LPF and definition of the complex quotient when extracting the phase difference image PD(x) without changing the size of the phase difference. Accordingly, in order to correspond to this, particularly, the definition is set so that the sign is negative with respect to a venous blood. Further, the γ is a positive proportion integer, and for example, corresponds to a gyromagnetic ratio of hydrogen.

(3) Determining Process

Next, an area interested by the user of the MRI device 1 (hereinafter, referred to as an area of interest) is set with respect to the phase difference image, and a predetermined operation process is performed with respect to the phase difference image included in the corresponding area of interest. Normality (or abnormality) of the tissue included in the area of interest may be determined by the operation process.

Figure 4:
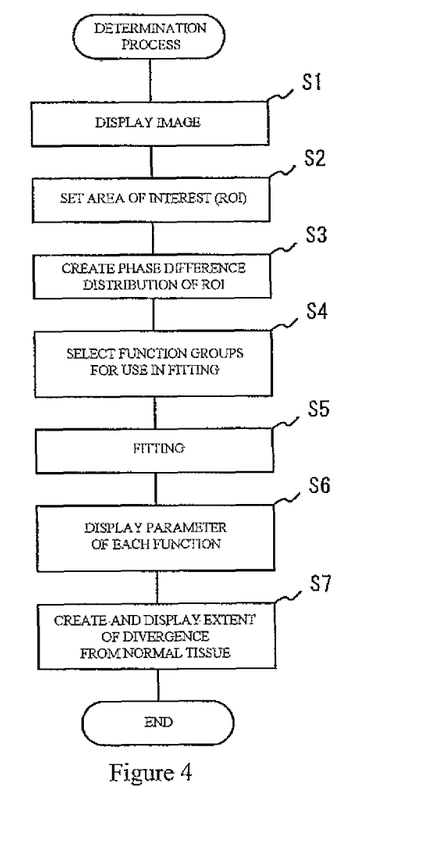
FIG. 4 is a flowchart illustrating a flow of determining whether a tissue is normal or not within an area of interest according to one or more embodiments.

Hereinafter, referring to FIG. 4, the process for determining the normality (or abnormality) of the tissue included in the area of interest will be described. The data processing illustrated in FIG. 4 is performed by the control system 20 under the control of the operation unit 26A. The operation unit 26A receives the instruction from the user to start an operation of the data processing illustrated in FIG. 4, when the creation of the phase difference image is completed.

[Displaying of Area Definition Interface]

When the processing starts, an interface for defining a cross section or a part of a space imaged in the MRI device 1 is displayed on a screen of the display unit 26C (S1). The interface may display the intensity image, the phase image, or the like created on the basis of the MR signal and defines a predetermined area on the image by an area definition means such as a closed curve (an edge and the like) or a coordinate value.

[Setting of Area of Interest]

Next, an operator of the MRI device 1 defines the cross section or the part of the space imaged in the MRI device 1 as the area through the interface displayed on the display unit 26C (S2). Here, the area defined by the operator is the area of interest. The operator defines an area supposing that an abnormal tissue may be included as the area of interest when the image displayed on the display unit 26C is observed. Further, the area of interest may be a 2-dimensional space or a 3-dimensional space.

[Creating Phase Difference Distribution]

When the area of interest is set, the operation unit 26A obtains the entire phase data of the MR signals obtained from the tissue included in the area of interest, and compiles statistics on the phase data to create the phase difference distribution in which a horizontal axis is set as a phase value and a vertical axis is set as a data number (S3).

Next, a function group using for fitting the phase difference distribution is selected (S4). Here, the operator selects a proper function group according to a target tissue, lesions, a disease condition, an imaging method, or the like. Further, in the case where an object is predetermined, step S4 is skipped, and a basic function group according to the target may be automatically applied. Further, the basic function group is prepared according to a target tissue, lesions, a disease condition, an imaging method, or the like, and a proper function group according to the object may be selected by selecting the object from a selection screen.

[Fitting]

Next, with respect to one phase difference distribution created in one area of interest, fitting is simultaneously performed by a plurality of functions (S5). That is, one phase difference distribution is close to a curve of overlaying the plurality of functions. In the plurality of functions, various functions may be adopted, and a Gauss distribution, a Lorentz distribution, a binomial distribution, or the like are exemplified.

Of course, the plurality of functions is not necessarily limited to the distribution functions, and need not be orthogonal to each other. Further, the plurality of functions may be configured by combining different kinds of functions. Further, when the fitting is performed by an operation of a computer, the plurality of functions is required to be finite.

Here, at least one of a plurality of functions used in the fitting may use the Gauss distribution. A signal distribution obtained by any tissue is a random variable represented by a sum of a plurality of independent factors, and secured to follow the Gauss distribution by a central limit theorem.

Each function used for the fitting has one to a plurality of parameters for changing a function shape, when the fitting is performed by using the plurality of functions, at least, it is necessary to adjust parameters larger than or equal to the number of functions used for fitting.

Actually, while the plurality of parameters is properly changed, a parameter set closest to overlapping of the phase difference distribution and the plurality of functions is searched. In this case, when the fitting function is the Gauss distribution, the parameter is small as three, and the parameters are easily adjusted. Further, the approximate degree of the plurality of functions and the phase difference distribution may be evaluated by, for example, a least-square method and the like.

In one or more embodiments to be described below, as the plurality of functions, a double Gauss distribution model having two Gauss distributions is adopted. Since the Gauss distribution has three parameters of a height, a central position (average), and a standard deviation $\sigma$ (or variance $\sigma^2$), in the double Gauss distribution model, the fitting is performed by adjusting six parameters.

The following Equation 2 represents a function used for fitting in the double Gauss distribution model.

[Equation 2]

$$f(\theta) = A_1 e^{-B_1(x-C_1)^2} + A_2 e^{-B_2(x-C_2)^2} \quad (2)$$

In the Equation 2, $A_1$ corresponds to a height of a first Gauss distribution, $B_1$ corresponds to a reciprocal number of variance of the first Gauss distribution, and $C_1$ corresponds to a central position of the first Gauss distribution. In addition, $A_2$ corresponds to a height of a second Gauss distribution, $B_2$ corresponds to a reciprocal number of variance of the second Gauss distribution, and $C_2$ corresponds to a central position of the second Gauss distribution.

[Display]

The parameter set obtained by fitting described above becomes the combination of values characterizing magnetic susceptibility of the tissue included in the area of interest. That is, a parameter set in the case where the area of interest includes an abnormal tissue having different magnetic susceptibility from the normal tissue is different from the parameter set in the case where the area of interest includes only the normal tissue.

Then, the parameter set obtained by fitting is displayed on the display unit 26C (S6), or the degree of deviation (normality (or abnormality) of the tissue) from the normal tissue of the tissue included in the area of interest is calculated on the basis of the parameter set to be displayed on the display unit 26C (S7). When the display is performed, the operator may obtain a reference for determining whether the tissue included in the area of interest is normal or abnormal, and obtain a reference of the deviation degree from the normal tissue.

[Description of Experimental Result]

Herein, a result of an experiment, in which with respect to the phase difference distribution obtained from a brain parenchyma of a mouse, fitting is performed in the double Gauss distribution model, will be described. In the experiment, in a mutant APP (Amyloid precursor protein) gene manipulated mouse with an amino acid substitution that causes an Alzheimer's disease in humans and a control mouse genetically controlled so that various properties are constant, the phase difference distribution in the brain was examined.

In detail, brains of the gene manipulated mouse and the control mouse are extracted and then imaged by using a 3D-FLASH (3D-Fast Low Angle Shot) with a 7T-MRI device to obtain the intensity image and the phase image at the same time. A main imaging condition is TR/TE: 50/12.8 ms, Flip Angle: 20°, Matrix Size: 194×128×82 (0.08 mm isovoxel), and adding: 24 times.

In the experiment, the intensity image and the phase image obtained from a cortex, a hippocampus, and a thalamus in the brain are used. Particularly, many senile plaques, as one of pathological changes of the Alzheimer's disease, are accumulated in the cortex, the hippocampus, and the thalamus. Further, it is known that iron is deposited in the senile plaques, and it is considered that a change in magnetic susceptibility due to the iron may be determined as the phase signal. In detail, the area of interest including a portion where the senile plaques exist is set, and with respect to the phase difference distribution of the phase value of each magnetic resonance signal collected from the brain parenchyma, the fitting is performed in the double Gauss distribution model.

Figure 5:
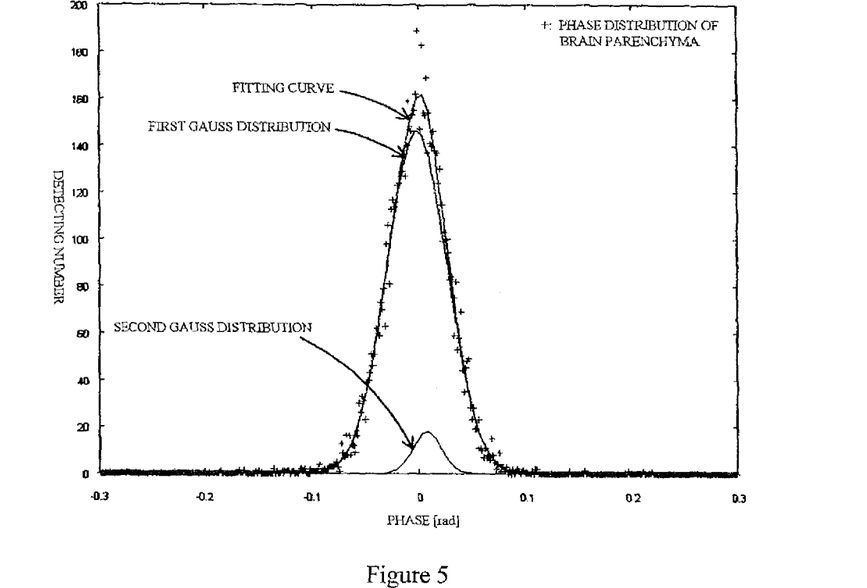
FIG. 5 is a graph illustrating fitting a phase difference distribution of a normal tissue according to one or more embodiments.
Figure 6:
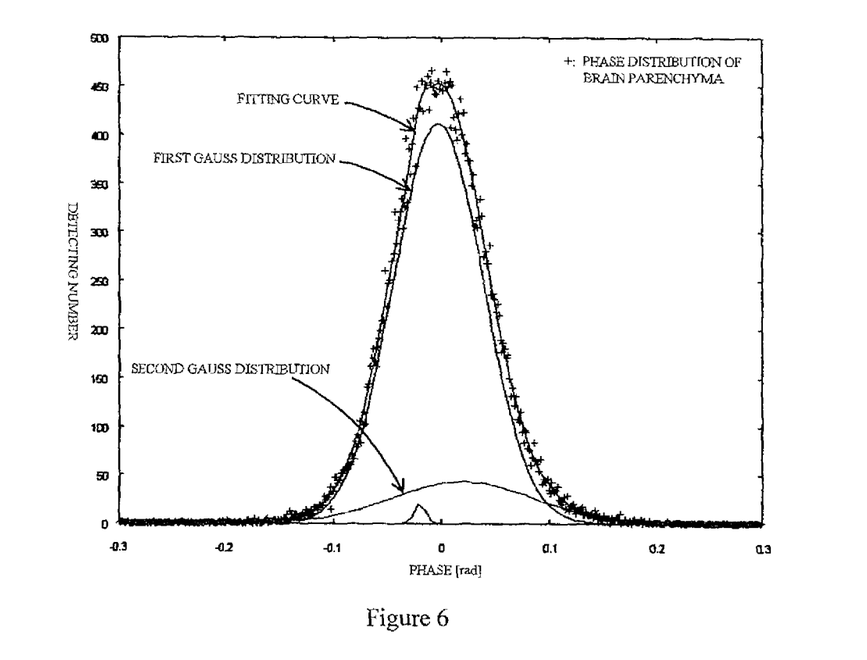
FIG. 6 is a graph illustrating fitting a phase difference distribution of an abnormal tissue according to one or more embodiments.
Figure 7:
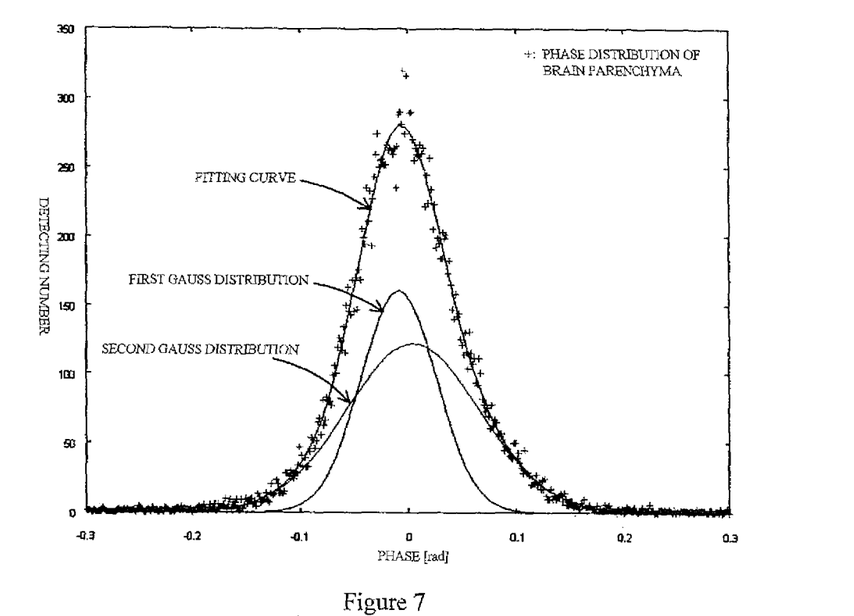
FIG. 7 is a graph illustrating fitting a phase difference distribution of an abnormal tissue according to one or more embodiments.

FIG. 5 is a graph illustrating a phase obtained from an area of interest set in the control mouse, and FIGS. 6 and 7 are graphs illustrating a phase obtained from the area of interest in the gene manipulated mouse. In the graphs, a horizontal axis represents a phase (radian), and a vertical axis represents a detecting number (for example, pixel number). Further, the phase value is adjusted in a range of $-\pi$ to $\pi$ by removing the phase wrapping as described above, but in FIGS. 5 to 7, the vicinity of the center (phase is 0) of the phase difference distribution is enlarged.

Here, when comparing contribution ratios (heights) of the Gauss distributions in a fitting curve, in FIG. 5, the first Gauss distribution has a height 7 to 8 times larger than the second Gauss distribution, and in FIG. 7, the first Gauss distribution has a height substantially the same as the second Gauss distribution. However, in FIG. 6, like FIG. 5, the first Gauss distribution has a height 8 to 9 times larger than the second Gauss distribution. That is, it can be seen that the contribution ratio (height) of each Gauss distribution may not be adopted as a determining reference of the existence of the abnormal tissue because each case varies even in the same lesion.

Next, when comparing standard deviations (widths) of the Gauss distributions, in FIG. 5, both the first Gauss distribution and the second Gauss distribution represent sharp distributions, and particularly, the second Gauss distribution has a width (for example, half width) smaller than the first Gauss distribution, or any Gauss distribution has a width (for example, half width) smaller than the phase difference distribution. Meanwhile, in FIGS. 6 and 7, the second Gauss distribution has a width (for example, half width) larger than the first Gauss distribution, and further, the second Gauss distribution has a width (for example, half width) larger than the phase difference distribution. That is, it can be seen that the standard deviation (width) of the Gauss distribution may be a determining reference of the existence of the abnormal tissue because a clear difference is observed in the normal tissue of the control mouse and the tissue including the senile plaque of the gene manipulated mouse.

The following discussion is made based on the above experimental results.

First, it is considered that the first Gauss distribution configuring the fitting curve illustrated in FIGS. 5 to 7 is caused by a noise component. It is expected that an error occurs in the phase difference due to a thermal electrical noise, a digital rise noise generated by cutting, or the like. It is known that the noises follow the Gauss distribution, and it is considered that a relatively high Gauss distribution occurs. Accordingly, in the case where the phase difference distribution is fit with the plurality of functions, it is considered that when the Gauss distribution is adopted in at least one of the plurality of functions, a good fitting result may be obtained.

Further, it is considered that the second Gauss distribution illustrated in the fitting curve illustrated in FIGS. 6 and 7 is related to a tissue including any magnetic material. The phase difference distribution illustrated in FIGS. 6 and 7 is obtained from the area of interest set so that the senile plaque is included. The senile plaque is the tissue including iron having magnetism as described above, and has a relatively large standard deviation when the phase difference distribution of the tissue including a magnetic material is fit with the Gauss distribution.

Further, when comparing cuffs of the phase difference distributions in FIGS. 5, 6, and 7, the phase difference distribution illustrated in FIG. 5 has a sharp increase relatively close to the Gauss distribution, but the phase difference distribution illustrated in FIGS. 6 and 7 have a wide cuff as compared with the Gauss distribution at the same height, and any broad phase difference distribution coexists. That is, it is suggested that when the cuff of the phase difference distribution is wider than that of the Gauss distribution at the same height, a tissue including any magnetic material is included in the area of interest.

Further, it is considered that when the Gauss distribution of which a center is shifted to the + side is fit, the tissue including a magnetic material in which the phase is shifted to the + side, and it is considered that when the Gauss distribution of which a center is shifted to the − side is fit, the tissue including a magnetic material in which the phase is shifted to the − side. As a result, it may be considered that overlapping of a distribution of the magnetic susceptibility of the normal tissue and the distribution of the magnetic susceptibility of the abnormal tissue becomes a distribution of the phase image.

Further, a difference in center between the phase difference distribution and the second Gauss distribution is large in FIGS. 6 and 7, as compared with FIG. 5. For the reason, when the phase difference of the normal tissue is 0, the Gauss distribution having a center close to the phase difference of 0 is considered as the Gauss distribution represented by the normal tissue, and the Gauss distribution having the center far away from the phase difference of 0 is considered as a tissue having high possibility that a large amount of tissue other than the normal tissue is included. That is, it is considered that a distance between a center of the Gauss distribution corresponding to the normal tissue and a center of the Gauss distribution corresponding to the abnormal tissue becomes a reference indicating normality (or abnormality) of the tissue included in the area of interest.

(4) Creating of Shape Image

Next, a phase difference enhancement imaging method of enhancing a specific phase difference, which is performed by using a fitting function obtained by using a double Gauss distribution model, will be described. Further, the phase difference enhancement imaging method is a method of expressing an image portion corresponding to phase information selected by enhancement by an enhancement function $w(\theta)$ on the intensity image $M(x)$, by selecting a part of the obtained phase difference image $PD(x)$ and selecting the part or all thereof. According to the phase difference enhancement imaging method, an image created by the enhancement function $w(\theta)$ may be provided.

Figure 8:
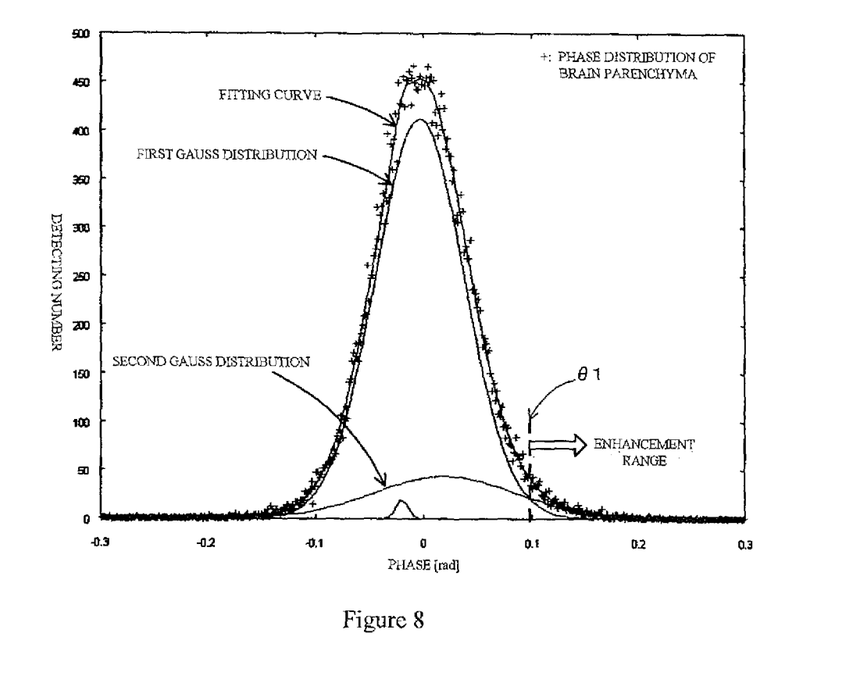
FIG. 8 is a diagram illustrating a relationship between a fitting function obtained by a double Gauss distribution model and a phase difference to be enhanced according to one or more embodiments.

FIG. 8 is a diagram illustrating a relationship between a fitting function obtained by a double Gauss distribution model and a phase difference to be enhanced. Further, in FIG. 8, an experimental result of FIG. 6 is exemplified, and the phase range to be enhanced is illustrated. In FIG. 8, when a phase where the second Gauss distribution and the first Gauss distribution cross each other is set to $\theta 1$, a phase range ($\theta > \theta 1$) where the second Gauss distribution is larger than the first Gauss distribution is the enhancement range.

In the double Gauss distribution model, as described above, in the case where the abnormal tissue including the magnetic material is included in the area of interest, the second Gauss distribution has a larger standard deviation and a wider base than the first Gauss distribution. Accordingly, it is considered that the second Gauss distribution indicating the distribution of the abnormal tissue enhances the tissue having a phase larger than or equal to the first Gauss distribution indicating the distribution of the normal tissue to provide a shape image with improved visibility ease of the abnormal tissue.

(Creating Phase Difference Image $PD(x)$)

Figure 10:
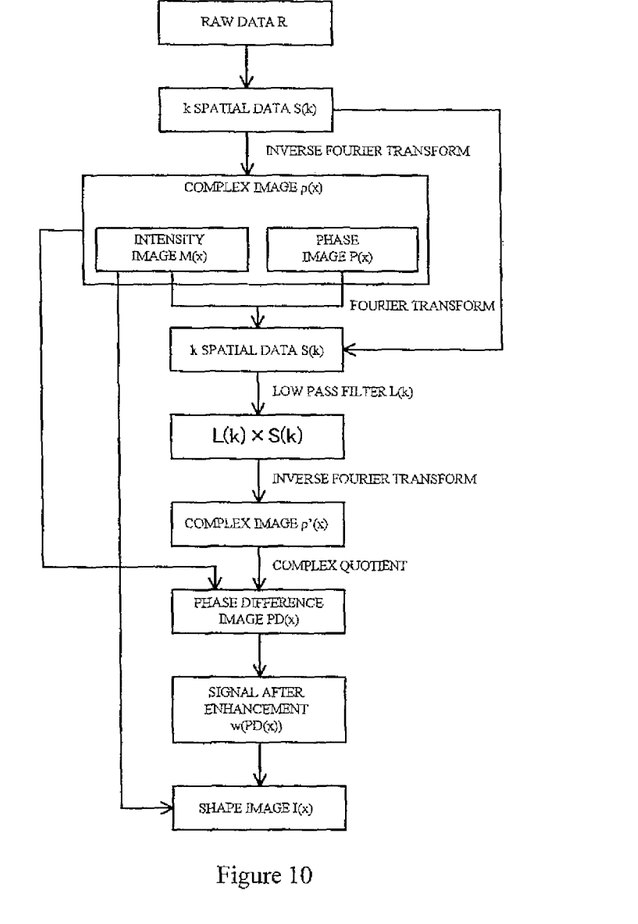
FIG. 10 is a diagram illustrating a flow of data processing until a shape image is created according to one or more embodiments.

FIG. 10 is a diagram illustrating a flow of data processing until a shape image is created. First, the operation unit 26A selects a phase in which the phase $\theta$ of the phase difference image $PD(x)$ is larger than $\theta 1$ to enhance the selected phase $\theta$.

Figure 9:
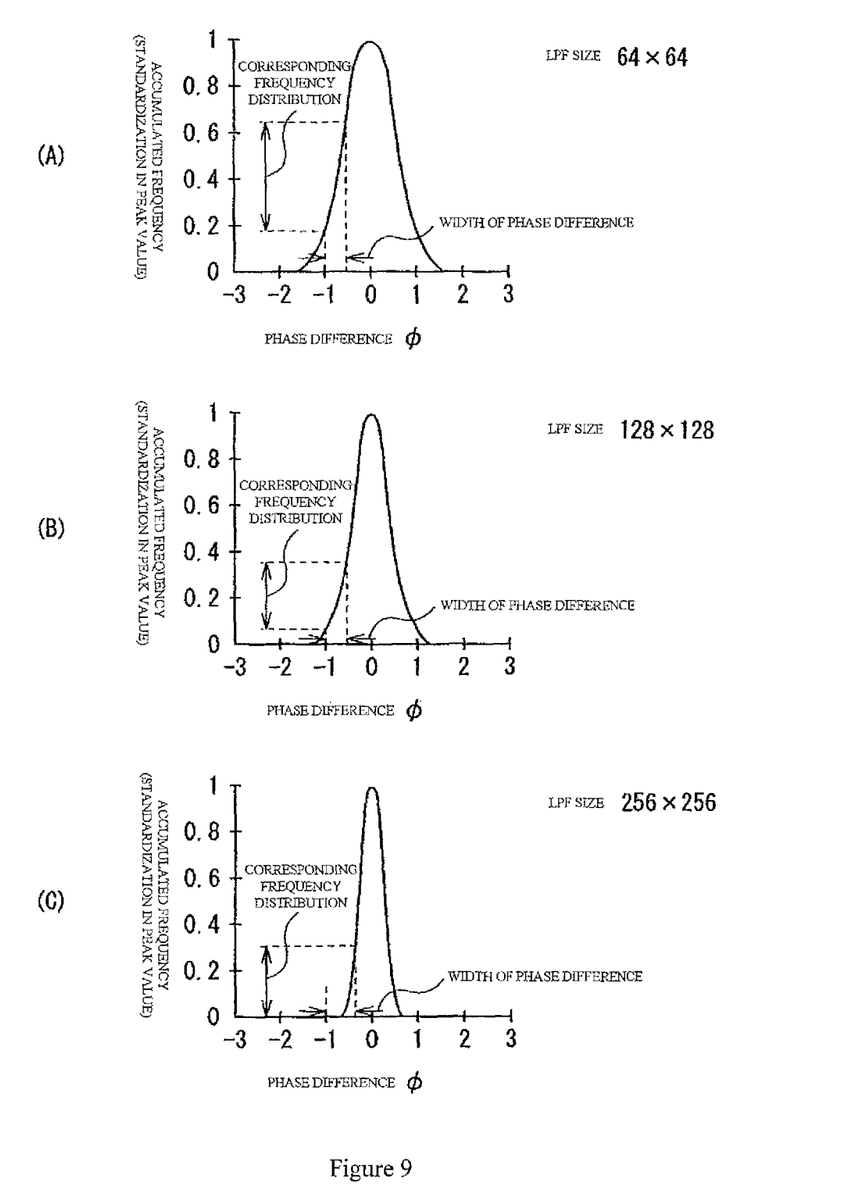
FIGS. 9(A)-(C) are schematic diagrams for describing a relationship between a phase difference distribution and an LPF size according to one or more embodiments.

The phase difference distribution is changed, for example, like models illustrated in FIGS. 9A to 9C, by a change in the LPF size. That is, a width of the phase difference distribution which is substantially symmetrical based on the phase difference of zero is reduced while the LPF size is increased. As a result, the phase difference image mainly has a value of the zero phase difference and a value near the zero phase difference, and thus a contrast of the tissue is hardly given as the phase difference image. Meanwhile, with respect to a tissue having a minute structure, in the case of using a large LPF, the contrast is easy to be given as compared with a case of using a small LPF.

The phenomenon is easily understood when considering that the complex quotient used when the phase difference image is obtained corresponds to the subtraction on the index. That is, with respect to $\exp(\phi-\phi')(\phi$: entire phase including phase wrapping, and $\phi'$: phase of a low pass component (low frequency component) including phase wrapping), in the case where the LPF size becomes the overall image size, all the frequencies are included, and as a result, when $\phi = \phi'$, the phase difference may be close to zero. Accordingly, the width of the phase difference distribution is decreased.

However, this is only an extreme trend, and in a general tissue, it is actually impossible to expect which distribution becomes in the case of using any filter. In order to respond to the change in the phase difference distribution, in one or more embodiments, the distribution flexibly responsible as the enhancement function to be described below is selected, and as illustrated in FIGS. 9A to 9C, the distribution having different frequency distributions with respect to the same phase difference have the same contrast.

For example, the operation unit 26A selects a width of the phase difference and a central value thereof so that the contrast of the target tissue has a desired size. Further, the selecting of the width of the phase difference and the central value thereof may be performed by not the operation unit 26A but the user of the MRI device 1. In this case, the operation unit 26A selects the phase $\theta$ of the target tissue to which the change of the phase difference distribution) by filtering is added.

Subsequently, the operation unit 26A enhances the selected phase $\theta$ with the enhancement function $w(\theta)$ to obtain an enhancement image $w(PD(x))$.

Here, as the enhancement function $w(\theta)$, an exponential function is used. In one or more embodiments, an example of the exponential function uses a $\pi$ function. The $\pi$ function is represented by the following two Equations.

$$w(\theta)=1 \ldots (-\sigma \leq \theta \leq \sigma)$$

$$w(\theta)=\exp(-a \times (Abs(\theta)-\sigma)^b) \ldots (\theta \text{ is beyond the above range})$$

(Determination of a, b, and σ)

All the parameters a, b, and σ have real values. The parameters a and b are to adjust the degree of the phase difference enhancement, and determined by the filter size of the LPF. The parameters a and b are determined so as to maximize a contrast C or a contrast noise ratio CNR of the target tissue and the background thereof. The parameter σ is to reduce a noise on the phase difference image PD(x), and determined by a standard deviation of a tissue in which a phase average value on the phase difference image PD(x) is near 0 (zero). The parameter σ may be required based on the data obtained from many experiments. However, the tissue in which the phase average value is near 0 (zero) may not exist on all the phase difference images PD(x) imaged at one time. In this case, the parameter σ is determined by, for example, the contrast C or the contrast noise ratio CNR.

Further, the aforementioned contrast C is determined by representing a difference between a signal w(PD(x1))×M(x1) after enhancing the target tissue at a position x1 on the image and a signal w(PD(x2))×M(x2) of a background of the tissue enhanced at a position x2 on the image as an absolute value, as illustrated in the following Equation.

Further, the contrast C—the contrast noise ratio CNR is represented by c/σ' as illustrated in the following Equation. Further, σ' is determined by a standard deviation on the enhancement image of the target tissue or a standard deviation on the enhancement image of the background of the target tissue.

However, when the σ' is determined, the aforementioned standard deviation may not be adopted. In this case, a standard deviation of an external signal of the subject 2 or a standard deviation according to a difference method may be adopted. Only the noise portion of the phase difference may be removed by using the π function defined by σ determined as described above to create the phase difference enhancement image having a high S/N ratio.

$$C=\text{Abs}(w(PD(x1))\times M(x1)-w(PD(x2))\times M(x2))$$

$$CNR=C/\sigma'$$

Further, Abs(θ) represents an absolute value of θ. The π function is a function in which the phase difference image PD(x) is not enhanced in the range of Abs(θ)≤σ, but enhanced in another range. Since the π function may be approximated to any power function with any precision, as compared with a case of using a polynomial expression as the enhancement function, more flexible enhancement may be performed.

For example, when the filter size of the LPF is changed according to a size of the imaging area, the distribution of the phase difference is slightly changed according to the change in size. Meanwhile, when the filter size of the LPF is changed while the size of the imaging area is constantly fixed, the distribution of the phase difference is largely changed according to the change in size. As such, in the case where imaging conditions and the like are different from each other, the distributions of the phase difference are different from each other. Accordingly, in the case of always using the same enhancement function regardless of the imaging condition and the like, each contrast is changed, and thus the enhancement of the target tissue may not be clearly performed. Meanwhile, in one or more embodiments, as described above, the parameters a, b, and σ of the enhancement function have real values to be flexibly changed according to the imaging condition and the like. Accordingly, even though the imaging condition is changed, the contrast may be equally or equivalently maintained.

(Creation of Shape Image I(x))

Next, the operation unit 26A, for example, masks the intensity image M(x) to the enhancement image w(PD(x)) according to a predetermined mode (rule) to obtain a shape image I(x). A detailed condition when masking the intensity image M(x) to the enhancement image w(PD(x)) may be set according to a target to be enhanced, and basically, may be set according to four kinds (tissue enhancement, vascular enhancement, entire enhancement, and structure enhancement) of enhancement modes to be exemplified below.

For example, as both the parameter a and the phase difference image PD(x) are positive or negative, any one of the tissue enhancement and the vascular enhancement may be selected. The entire enhancement does not depend on the signs of the parameter σ and the phase difference image PD(x), but in the structure enhancement, for example, a value of a phase difference α (hereinafter, simply referred to as a phase difference α) made by a structure in the cortex is obtained by an experiment in advance, and a conditional expression is set according to a size relation between the phase difference α and the phase difference image PD(x).

Enhancement mode A (tissue enhancement)

$$I(x)=w(PD(x))\times M(x) \ldots (PD(x)\geq 0)$$

$$I(x)=M(x) \ldots (PD(x)<0)$$

Enhancement mode B (vascular enhancement)

$$I(x)=w(PD(x))\times M(x) \ldots (PD(x)\leq 0)$$

$$I(x)=M(x) \ldots (PD(x)>0)$$

Enhancement mode C (entire enhancement)

$$I(x)=w(PD(x))\times M(x)$$

Enhancement mode D (structure enhancement)

$$|\alpha|<\sigma$$

When PD(x)≤0, $$I(x)=w(PD(x))\times M(x) \ldots (-|\alpha|\leq PD(x)\leq -\sigma)$$

$$I(x)=M(x) \ldots (PD(x)<-|\alpha|)$$

When PD(x)>0, $$I(x)=w(PD(x))\times M(x)$$

In the enhancement mode A, the operation unit 26A extracts a portion where the phase difference image PD(x) is 0 (zero) or more and enhances only the portion to create the shape image I(x). In this case, the portion where the phase difference image PD(x) is negative may not be enhanced. In the enhancement mode A, the shape image I(x) becomes the tissue enhanced image.

In the enhancement mode B, the operation unit 26A extracts a portion where the phase difference image PD(x) is 0 (zero) or less and enhances only the portion to create the shape image I(x). In this case, the portion where the phase difference image PD(x) is positive may not be enhanced. In the enhancement mode B, the shape image I(x) becomes the blood vessel enhanced image.

In the enhancement mode C, the operation unit 26A creates the shape image I(x) by enhancing the entire phase difference image PD(x). In the enhancement mode C, the shape image I(x) becomes the entirely enhanced image including the tissue, the blood vessel, and the like.

In the enhancement mode D, the operation unit 26A enhances a portion filling −|α|≤PD(x)≤−σ when the phase difference image PD(x) is 0 (zero) or less to create the shape image I(x). In this case, the portion filing PD(x)<−|α| is not enhanced. Further, the operation unit 26A creates the shape image I(x) by using the conditional expression described above even when the phase difference image PD(x) is larger than 0 (zero). In the enhancement mode D, the shape image I(x) becomes the structure enhanced image. Further, since the phase difference α is made by the structure in the cortex, the shape image I(x) actually becomes the image in which the cortex structure is enhanced.

As such, in one or more embodiments, an anatomical location of the brain function against the tissue contrast expressed by each shape image I(x) may be more accurately specified by changing a masking method of the enhancement images w(PDr(x)) and w(PDa(x)) and the intensity image M(x).

(5) Summary

According to one or more embodiments described above, when analyzing an MR image obtained from a living body, the phase difference distribution of an MR signal obtained from an area of interest is created, the phase difference distribution is simultaneously fit with a plurality of function groups, and normality of the living body included in the area of interest is verified based on the magnetic susceptibility of the tissue included in the area of interest which is determined on the basis of the parameters of the plurality of function groups fit to the phase difference distribution. Accordingly, a tissue or lesions, which cannot be portrayed by means of medical imaging equipment such as an MRI, may be realistically detected within the current range of health care services provided under medical insurance.

Further, the technology is not limited to the aforementioned embodiments or modified example, but includes components acquired by substituting the respective components disclosed in the aforementioned embodiments or modified example with each other or changing combinations of the respective components, components acquired by substituting the respective components disclosed in known technology and the aforementioned embodiments or modified example with each other or changing combinations of the respective components, and the like. In addition, the technical scope of the present invention is not limited to the aforementioned embodiments and includes details disclosed in the appended claims and equivalents thereto.

It is considered that the technique may be used for various diagnoses using the MRI. Particularly, the technique may be largely contributed when detecting a fine lesion or tissue such as amyloid β. Even in the case where those diffusely present in the tissue are detected, the method may be applied, and for example, a ratio of fat included in the liver to be necessarily examined in the medical examination and the like may be quantitatively measured.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

REFERENCE SIGNS LIST

1 . . . MRI device, 2 . . . Subject, 10 . . . Coil system, 10 A . . . bore, 11 . . . Static magnetic coil portion, 12 . . . Inclined magnetic coil portion, 13 . . . Radio frequency (RF) coil portion, 20 . . . Control system, 21 . . . Static magnetic power supply, 22 . . . Inclined magnetic power supply, 23 . . . Transmitting unit, 24 . . . Receiving unit, 25 . . . Sequence controller, 26 . . . Information processing device, 26A . . . Operation unit, 26 B . . . Input unit, 26 C . . . Display unit, 26 D . . . Memory unit, 27 . . . Program, 30 . . . Bed portion, 13-1~13-8 . . . Coil

The invention claimed is:

1. An image analysis device for analyzing a magnetic resonance image obtained from a living body, comprising:
a central processing unit (CPU) that:
creates a phase difference distribution of a magnetic resonance image obtained from a predetermined area of the living body;
fits the phase difference distribution with a plurality of function groups; and
verifies normality of the living body included in the predetermined area, based on the magnetic susceptibility of the tissue included in the predetermined area determined on the basis of the parameters of the plurality of function groups fit to the phase difference distribution,
wherein a horizontal axis is set as a phase value and a vertical axis is set as a data number in the phase difference distribution.

2. The image analysis device of claim 1, wherein the plurality of function groups includes at least one Gauss distribution.

3. The image analysis device of claim 1, wherein
the plurality of function groups includes a first and second Gauss distributions,
the first Gauss distribution has a larger standard deviation than the second Gauss distribution, and
the CPU further creates a magnetic resonance image enhancing a pixel having a phase in which the first Gauss distribution is larger than the second Gauss distribution.

4. An image analysis method for analyzing a magnetic resonance image obtained from a living body, comprising:
creating a phase difference distribution of a magnetic resonance image obtained from a predetermined area of the living body;
fitting the phase difference distribution with a plurality of function groups; and
verifying normality of the living body included in the predetermined area, based on the magnetic susceptibility of the tissue included in the predetermined area determined on the basis of the parameters of the plurality of function groups fit to the phase difference distribution,
wherein a horizontal axis is set as a phase value and a vertical axis is set as a data number in the phase difference distribution.

5. A non-transitory computer readable medium storing an image analysis program for implementing a function of analyzing a magnetic resonance image obtained from a living body in a computer, wherein the program comprises functionality to:
create a phase difference distribution of a magnetic resonance image obtained from a predetermined area of the living body;
fit the phase difference distribution with a plurality of function groups; and
verify normality of the living body included in the predetermined area, based on the magnetic susceptibility of the tissue included in the predetermined area determined on the basis of the parameters of the plurality of function groups fit to the phase difference distribution,
wherein a horizontal axis is set as a phase value and a vertical axis is set as a data number in the phase difference distribution.

6. The image analysis device of claim 2, wherein
the plurality of function groups includes a first and second Gauss distributions,
the first Gauss distribution has a larger standard deviation than the second Gauss distribution, and
the CPU further creates a magnetic resonance image enhancing a pixel having a phase in which the first Gauss distribution is larger than the second Gauss distribution.

* * * * *